United States Patent
Raybuck

(10) Patent No.: US 6,695,004 B1
(45) Date of Patent: Feb. 24, 2004

(54) MAGNETIC AUTOMATIC STOP VALVE

(75) Inventor: John L. Raybuck, Durham, NC (US)

(73) Assignee: Alaris Medical Systems, Inc., San Diego, CA (US)

(*) Notice: Subject to any disclaimer, the term of this patent is extended or adjusted under 35 U.S.C. 154(b) by 0 days.

(21) Appl. No.: 10/321,249

(22) Filed: Dec. 16, 2002

(51) Int. Cl.⁷ ............ F16K 31/22; F16K 33/00; A61M 5/14; A61M 39/22
(52) U.S. Cl. ............ 137/433; 137/15.26; 137/399; 141/198; 222/67; 251/65; 604/254
(58) Field of Search ............ 137/15.26, 192, 137/302, 399, 430, 433; 141/198; 222/67; 251/65; 604/247, 251, 254

(56) References Cited

U.S. PATENT DOCUMENTS

| | | | |
|---|---|---|---|
| 2,538,662 A | 1/1951 | Abbott | 137/430 |
| 2,691,386 A | 10/1954 | Madison | 137/400 |
| 2,784,733 A * | 3/1957 | Martinez | 137/433 |
| 2,879,784 A | 3/1959 | Cutter | 137/192 |
| 3,105,511 A | 10/1963 | Murphy, Jr. | 137/399 |
| 3,207,372 A * | 9/1965 | Evans | 604/254 |
| 3,233,625 A | 2/1966 | Pase | 137/416 |
| RE26,124 E | 12/1966 | Koehn | 604/254 |
| 3,467,135 A | 9/1969 | Muskalla | 137/410 |
| 3,980,457 A * | 9/1976 | Smith | 251/65 |
| 3,989,043 A | 11/1976 | Dimeff | 137/430 |
| 4,175,558 A * | 11/1979 | Hess, III et al. | 222/67 |
| 4,353,523 A * | 10/1982 | Palti | 251/65 |
| 4,562,855 A * | 1/1986 | Cummings et al. | 251/65 |
| 4,769,007 A * | 9/1988 | Hsu | 604/251 |
| 4,967,789 A * | 11/1990 | Kypris | 251/65 |
| 5,014,735 A * | 5/1991 | Cummings | 137/195 |
| 5,176,167 A * | 1/1993 | Tiao | 137/430 |
| 5,527,295 A | 6/1996 | Wing | 604/254 |
| 5,655,568 A * | 8/1997 | Bhargava et al. | 251/65 |
| 5,730,730 A * | 3/1998 | Darling, Jr. | 604/254 |
| 5,983,919 A * | 11/1999 | Ottinger et al. | 251/65 |
| 6,019,114 A * | 2/2000 | Rodgers | 222/67 |
| 6,213,986 B1 | 4/2001 | Darling, Jr. | 604/248 |
| 6,325,094 B1 * | 12/2001 | Rodgers | 137/433 |
| 6,619,341 B2 * | 9/2003 | Cushing | 141/198 |

* cited by examiner

*Primary Examiner*—George L. Walton
(74) *Attorney, Agent, or Firm*—Fulwider Patton Lee & Utecht, LLP

(57) ABSTRACT

A magnetic automatic stop valve formed in a container of a medical fluid administration system has one magnetic element located in a float and another magnetic element located proximate a valve seat. As the fluid level in the container decreases, the magnetic field established between the float and the valve seat eventually overcomes the buoyancy of the float in the fluid and attracts the float into the valve seat at which position the flow of fluid from the container is stopped. The float is formed of two identical halves each of which has one half of an internal post. When joined together to make the float, the internal post is fully formed and extends from one end of the float to the other. One magnetic element is slid over the post during manufacture and is free to slide from one end of the float to the other. Due to the symmetrical nature of the float and the freedom of movement of the internal magnetic element on the post, the float may be inserted into the fluid container without regard to which direction it faces thus lowering manufacturing costs. Flow seals are provided to completely shut off flow when the float is seated.

31 Claims, 8 Drawing Sheets

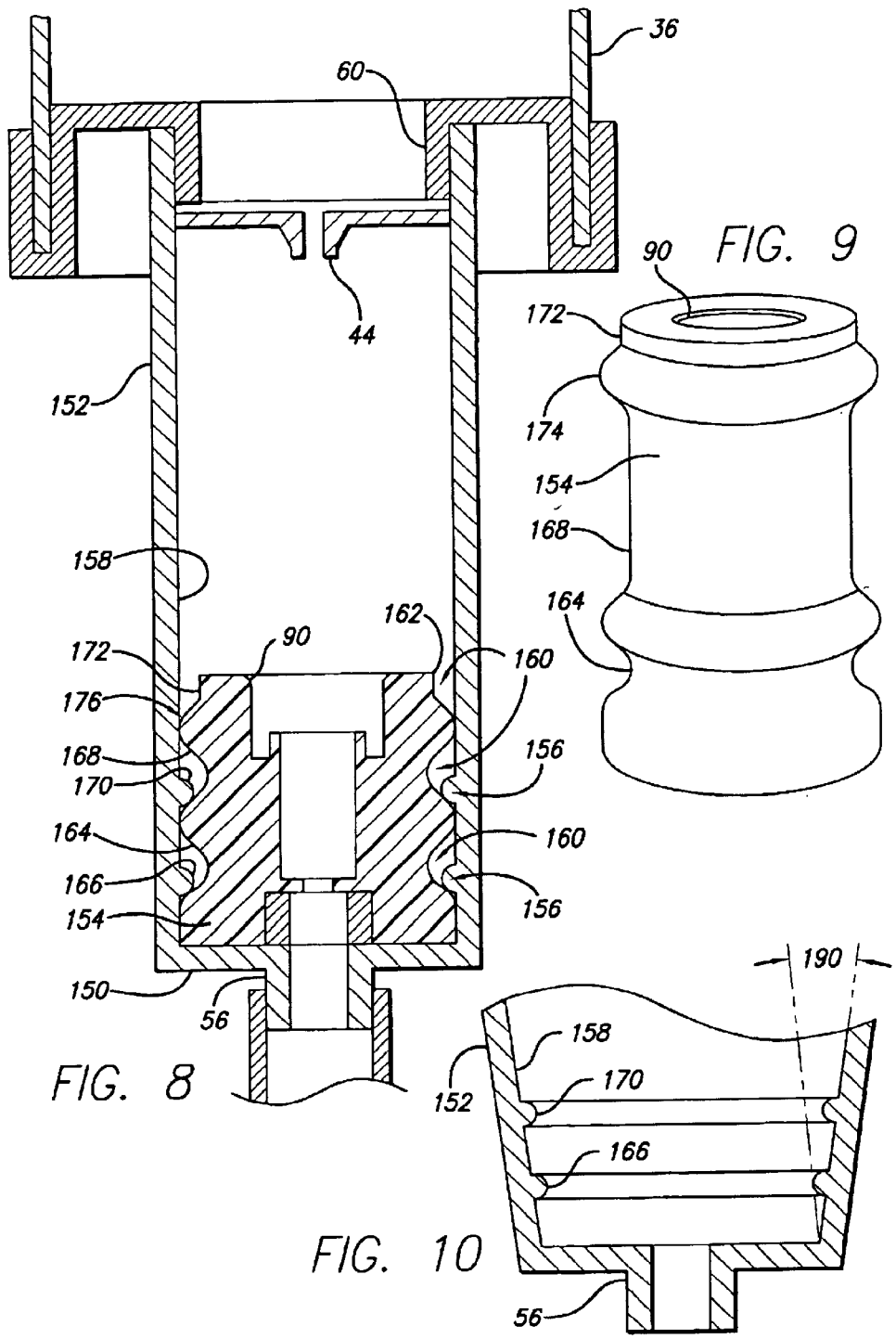

MAGNETIC AUTOMATIC STOP VALVE

BACKGROUND

The invention relates generally to medical fluid flow valves and more particularly, to valves that automatically shut off when fluid reaches a certain level.

During hospitalization, a physician may desire to infuse a medical fluid into a patient's bloodstream. The medical fluid may be for therapy, the replacement of body fluid, or for other purposes. During the administration of medical fluids to a patient, it is important that amounts of air exceeding a certain threshold not be infused. If too large a quantity of air is allowed to enter the patient's blood stream, an embolism could result, which can be a serious condition.

In infusing medical fluids, many times a medical fluid reservoir, such as a bag or bottle, is hung in an inverted position and its contents are allowed to infuse into the patient either through gravity or with the aid of an infusion pump that accurately controls the flow rate in accordance with the physician's instructions. A fluid administration set is used to conduct the fluid from the bag to the patient and comprises a fluid line that is connected to the inverted bag at one end, referred to as its proximal end, and is connected to a catheter inserted into the vein of a patient at the other end, referred to as its distal end. Many fluid infusion administration sets include a device known as a drip chamber. This device may include a sharpened spike for penetrating the stopper or septum of the inverted bag, bottle, or other type of container to gain access to the contents of that container. The spike conducts the contents of the container to a chamber that includes a precise drop former located at its inlet or upstream end. The drop former forms drops having a known quantity of liquid. The number of drops may be counted per unit of time to determine the flow rate of fluid into the patient. The drop former is located within a chamber in which the formed drops fall or "drip," and that chamber has an outlet, or downstream end, that connects to the tubing of the administration set. That tubing provides a conduit for the medical fluid to flow to the patient.

Nurses monitor the drip chamber for the presence of drops to be sure that the medical fluid reservoir has not emptied. As is well known to those skilled in the art, drip chambers are designed to continuously have a certain level of fluid within the chamber when the flow of fluid into the patient is proceeding normally, such as 3 ml. When the fluid in the reservoir and tube above the drip chamber is exhausted and drops cease to fall, the level of fluid in the drip chamber will decrease until eventually it is empty. Unless the administration set tubing is clamped or other action is taken, air may then enter the administration tubing to which the drip chamber is connected. Thus, an empty fluid reservoir may result in air being drawn into the drip chamber and tubing and consequently being infused into the patient unless the line is clamped or other action is taken.

Additionally, if the fluid level in the drip chamber is permitted to decrease too far, the nurse cannot replace the fluid reservoir with another unless the entire administration set is primed again to remove air that has found its way into the line. Priming the line takes time and it is desirable to provide devices that control the entry of air into the fluid line so that the procedure of re-priming is not necessary. In particular, it is desirable that enough fluid remain in the drip chamber when the present reservoir is exhausted so that a new fluid reservoir may be connected to the drip chamber and the flow of new fluid to the patient begin without the need for re-priming the fluid administration set.

In another application, the drip chamber may form a part of a burette and be located at the distal, or downstream, end of the burette chamber. In such a case, the drip chamber would not include a sharpened spike but would include the other elements discussed above. In yet a further arrangement, the drip chamber may not have a spike but may instead be fed at its upstream end by a length of tubing that has an integral spike for establishing communication with the container of medical fluid. The spike on the tubing is inserted into the container and the fluid flows through the short length of tubing into the drip chamber.

Nurses are very busy and it is desirable to provide a device that automatically shuts off flow when the medical fluid container becomes depleted. Therefore, those in the development of medical fluid infusion devices have created various shut off valves that have been incorporated directly into the drip chamber device to automatically shut off fluid flow through the fluid line once the medical fluid reservoir has emptied. Some of these systems are relatively complex while some are simpler. One class of such devices uses a device that floats in the liquid of the drip chamber and has a valve seat located at the downstream end of the drip chamber. As is typical in these designs, the floating device floats at a certain level in the fluid dependent upon the buoyancy of the floating device. The floating device is designed to seat when the fluid in the chamber decreases to a certain low level. As the level decreases, the float approaches nearer and nearer the valve seat until it finally seats and shuts off flow thereby providing an automatic shut off valve that does not require constant monitoring by a nurse.

Problems have arisen with such devices, one of which is that the floating device may not properly seat and completely shut off flow. Under adverse conditions, such as where the administration set may be moving from side to side or oriented at an angle other than directly vertical, the valve device may be slow in seating and fluid shut off may be delayed, thus raising the possibility that air may enter the administration line.

A variation in this type of automatic shut off valves has incorporated magnetic force to assist in fluid line shut off. The force of magnetic attraction is used between a float located in the drip chamber and a stationary part, such as a valve seat, to shut off fluid flow in the administration line. Such an approach has an advantage in that it acts as a latching-type of valve. That is, the magnetic field or fields used have a field strength that increases non-linearly as the distance between the magnetic devices decreases. While some attraction exists when the magnetic devices are relatively far apart from each other, that attraction increases as they near each other until finally, the magnetic force provided by their attraction overcomes the buoyancy of the float in the drip chamber and it is drawn into a seating position in this magnetically activated valve thus positively shutting off fluid flow.

This magnetic force developed between the two parts tends to hold the valve in the shut off position better than other valves that rely only on gravity. Where prior floats relied only on their weight to seal the fluid line, the use of a magnetic force as well as the weight of the float results in a better chance that the float will completely seal and shut off flow. The use of a magnetic force also tends to draw the float into the seat when the drip chamber is tilted out of vertical alignment. Once seated, the valve is "latched" in that some mechanical force beyond that provided by the mere buoyancy of the float developed by newly added fluid is required to separate the float from its valve seat. Even filling the drip chamber with fluid will typically not dislodge the float from the valve seat in these devices. The force of the magnetic attraction to the seat exceeds the force provided by the buoyancy of the float and some mechanical force is necessary to dislodge the two. Typically, the nurse will squeeze the wall of the drip chamber to dislodge the float from the valve seat so that it may rise to the level of the fluid.

However, problems have arisen in such devices. Magnetic devices comprising metallic elements should not be exposed to medical fluid in the infusion line. Additionally, some prior devices have uniquely shaped float devices that must be installed in a particular orientation in the drip chamber as the device is manufactured. Failure to properly orient the parts during manufacture can result in a valve that does not completely seal and may therefore need to be scrapped. Such requirements increase manufacturing costs. In other devices, the seal is formed between relatively rigid surfaces, and this configuration may give rise to the problem of leakage at the seal due to imperfections, or lack of fit, between the sealing surfaces. In yet another arrangement, the two devices comprising the valve, at least one of which is a magnet, may not be aligned so that the lines of magnetic flux between the two devices are then not optimally effective. In such a case, a larger magnet is used, which can increase costs.

Hence, a need has been recognized by those skilled in the art for an automatic shut off valve usable in fluid administration lines that is efficient and reliable in operation. A need has also been recognized for an improved automatic fluid shut off valve that uses magnetic force to assist in the shut off. Yet a further need has been recognized for a magnetic fluid shut off valve that is relatively easy to manufacture and has lower manufacturing costs. The present invention fulfills such needs and others.

SUMMARY OF THE INVENTION

Briefly and in general terms, the present invention is directed to an apparatus and method for a magnetic automatic shut off valve for use in regulating the flow of medical fluid. In a first aspect, an automatic shut off valve for use in regulating the flow of medical fluid comprises a container adapted to contain medical fluid, the container having an upstream end and a downstream end and defining an exit orifice at the downstream end, a hollow float defining an internal post, the float disposed within the container, a first attraction element disposed within the float and disposed over the post and adapted to slide along the post, and a second attraction element disposed at the exit orifice, the first and the second attraction elements being formed of materials that produce magnetic attraction between the two elements, wherein the materials that produce the magnetic attraction between the two elements are selected so that the strength of the magnetic attraction between the two elements is such that when the fluid in the container falls to a level near depletion, the first and second attraction elements are attracted to each other with sufficient force to move the float into a position that seals the downstream end against fluid flow.

In more detailed aspects, the automatic shut off valve further comprises a valve seat located proximate the exit orifice at the downstream end of the container, the valve seat having a first sealing surface, wherein the float includes a second sealing surface configured to mate with the first sealing surface and form the seal against fluid flow. A third sealing surface is disposed at a fixed position within the container at a selected location away from the first sealing surface, and a fourth sealing surface located on the float and configured to mate with the third sealing surface to provide a greater seal against fluid flow. The float has a section of increased diameter that forms the fourth sealing surface, wherein the section of increased diameter forming the third sealing surface is located substantially at the center of the float. Wherein the third sealing surface comprises a membrane of pliable material formed substantially in the shape of a ring and having a smaller inner diameter than an outer diameter of the fourth sealing surface of the float wherein the third sealing surface and the fourth sealing surface come into contact with each other thereby sealing against fluid flow when the float is disposed such that the first and second sealing surfaces are in contact.

In another aspect, the automatic shut off valve further comprises a first sealing surface disposed at a fixed position within the container proximate the exit orifice at the downstream end of the container, and a third sealing surface disposed at a fixed position within the container on a container wall at a selected location away from the first sealing surface, wherein the first and third sealing surfaces engage the float to form seals against fluid flow when the float is moved into the position that seals the downstream end against fluid flow due to the magnetic attraction between the two elements. The float includes opposite ends, each end of which includes a second sealing surface configured to mate with the first sealing surface, and the float includes a generally cylindrical section that provides a fourth sealing surface configured to mate with the third sealing surface, wherein the first and second sealing surfaces form a seal against flow and the third and fourth sealing surfaces form another seal against flow when the float has been moved into the position that seals the downstream end against fluid flow due to the magnetic attraction between the two elements.

In yet a further aspect, the float comprises two substantially identical halves joined together to form the float, each float half including a half of the post such that when the substantially identical float halves are joined together, the entire internal post is formed. The float is generally cylindrical with a larger diameter cylindrical section located at the longitudinal center of the float, the float includes opposing ends, and the first attraction element is disposed over the post such that it may freely slide along the post, whereby the float may be inserted into the container with either of the opposing ends facing the exit orifice at the downstream end of the container and the first attraction element will slide along the internal post towards the second attraction element to establish a magnetic interaction with the second attraction element.

In more detailed aspects, the first attraction element has an inner opening larger in diameter than the diameter of the post, and the outer diameter of the first attraction element has a size that is smaller than the inner diameter of the hollow float, whereby the first attraction element is free to slide along the post within the float.

In yet a further aspect, the float has a length that exceeds an inner diameter of the container.

In yet another more detailed aspect, at least one of the first and second attraction elements comprises a magnet with the strength of the magnetic force produced by the magnet selected so that the magnet will attract the float to the valve seat for shutting off flow when a selected level of fluid remains in the container. The strength of the magnetic force produced by the magnet is also selected so that the float will align itself with the valve seat when the container is disposed at an angle other than vertical.

In further aspects, the float has a longitudinal axis and is rotationally symmetrical about the longitudinal axis. The float is also symmetrical about a plane perpendicular to the float's longitudinal axis, the plane being located through the center of the float.

In accordance with method aspects, a method of automatically shutting off the flow of medical fluid from a container having an upstream end and a downstream end and defining an exit orifice at the downstream end comprises disposing a first attraction element over a post disposed within a hollow float so that the first attraction element may slide freely along the post, disposing a second attraction element at the exit orifice, the first attraction element and the second attraction element being formed from materials that produce magnetic attraction between the two elements, and inserting the float into the container so that, when fluid in the container falls to a level near depletion, the first and second attraction elements are attracted to each other with sufficient force to move the float into a position that seals the downstream end to fluid flow.

In further method aspects, the method further comprises forming the float from two substantially identical halves joined together, each float half including a half of the post such that when the substantially identical float halves are joined together, the entire internal post is formed. The method also comprises forming the float to be generally cylindrical with a larger diameter cylindrical section located at the longitudinal center, and with the float having opposing ends, and disposing the first attraction element over the post such that the first attraction element may freely slide along the post, whereby the float may be inserted into the container with either of the opposing ends facing the exit orifice at the downstream end of the container and the first attraction element will slide along the internal post towards the second attraction element to establish a magnetic interaction with the second attraction element.

Additional aspects of the method of automatically shutting off the flow of medical fluid comprise forming the float to have a length that exceeds an inner diameter of the container, and forming the first and second attraction elements so that at least one comprises a magnet, and selecting the strength of the magnetic force produced by the magnet so that the magnet will attract the float to the valve seat for shutting off flow when a selected level of fluid remains in the container. Further, the method comprises selecting the strength of the magnetic force produced by the magnet to align the float with the valve seat when the container is disposed at an angle other than vertical.

Further detailed method aspects include forming the float such that it is rotationally symmetrical about a longitudinal axis, and forming the float such that it is symmetrical about a plane perpendicular to the float's longitudinal axis, the plane being located through the center of the float.

Other features and advantages of the present invention will become more apparent from the following detailed description of the invention when taken in conjunction with the accompanying drawings.

BRIEF DESCRIPTION OF THE DRAWINGS

FIG. 8 presents a view of a drip chamber in which details of one embodiment of a valve seat mounting arrangement are shown, the drip chamber having inwardly-extending protrusions and the valve seat having external grooves for mating with the drip chamber protrusions to properly locate and retain the valve seat in the drip chamber, the combination of protrusions and grooves providing a fluid seal also, the drip chamber further having an inward taper extending towards the distal end of the drip chamber;

FIG. 9 presents another embodiment of a grooved shape of the outer surface of a valve seat, the shape of the outer surface selected not only to properly locate the valve seat in the drip chamber but also to provide a seal between the valve seat and the drip chamber wall to prevent fluid from flowing between the valve seat and the drip chamber wall; and FIG. 10 is an exaggerated schematic view showing the taper of the drip chamber, in particular, the drip chamber being tapered inwardly in the distal direction.

DETAILED DESCRIPTION OF THE PREFERRED EMBODIMENTS

Figure 1:
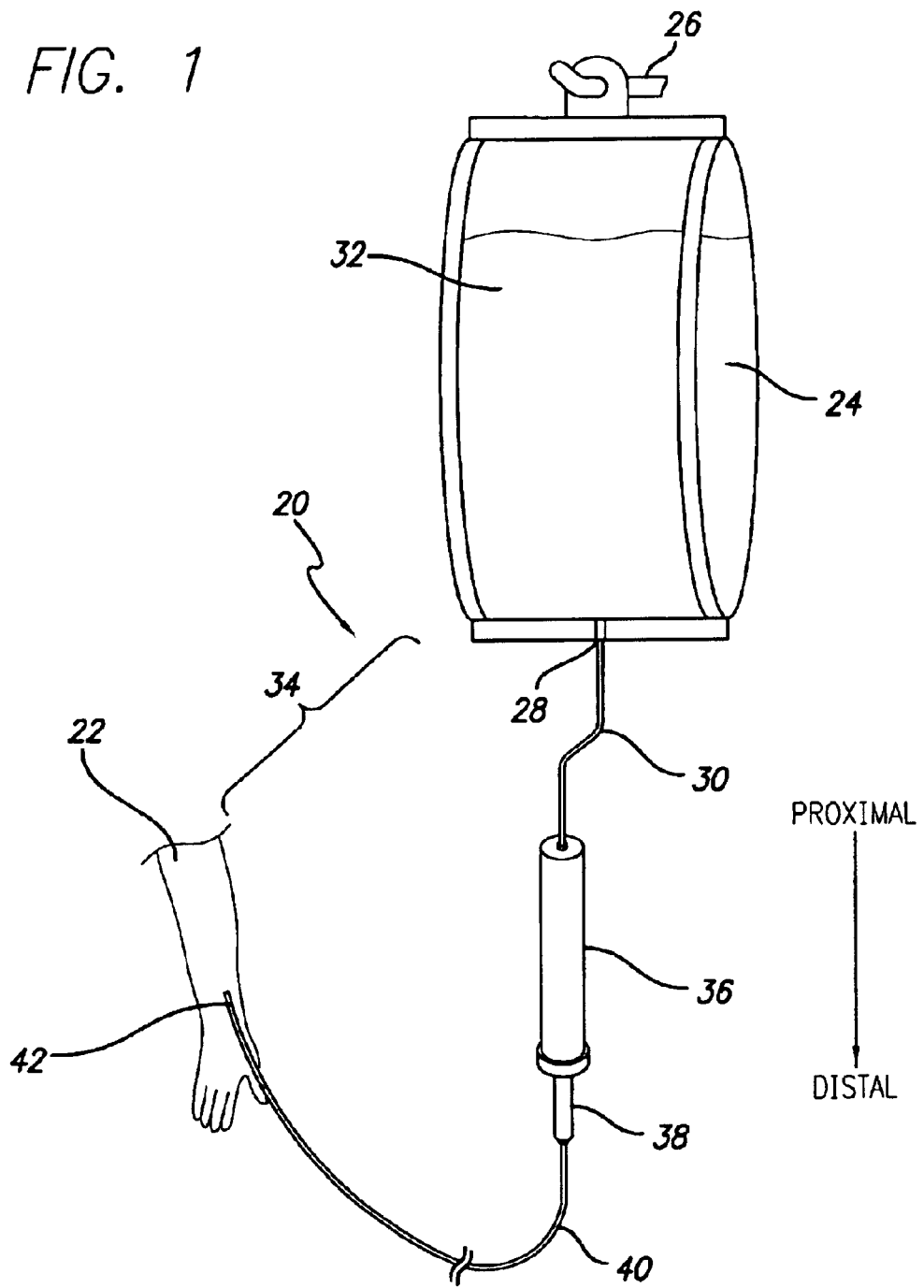
FIG. 1 is an overview of a fluid administration set interconnecting a medical fluid reservoir with a patient, the administration line of the set having a drip chamber located at the downstream end of a burette with a magnetic automatic shut off valve formed as an integral part of the drip chamber in accordance with aspects of the invention.

Referring now to the drawings with more particularity, wherein like reference numerals in the separate views refer to like or corresponding elements, there is shown in FIG. 1 an overview diagram of a medical fluid administration system 20 terminating in the vein of the arm of a patient 22. The diagram is not to scale. A medical fluid reservoir 24 is hung on a standard hanger 26, only a part of which is shown, above the level of the patient 22 so that a gravity feed system is provided. The reservoir in this case comprises a flexible bag but could as easily have been a bottle or other type of container. An access device 28 penetrates the stopper or septum of the bag to establish fluid communication between the bag and upstream tubing 30. In this case, a medical fluid administration set 34 is used and comprises the access device 28, the upstream tubing 30, a burette 36, a drip chamber 38 with an integral magnetic automatic shut off valve, downstream tubing 40, and a connection device 42 for a sharpened cannula (not shown) used to penetrate the patient's vein and establish fluid communication with his or her circulatory system. The bag access device 28 may take the form of a sharpened and vented spike that penetrates a closure of the bag in this embodiment. Thus the medical fluid 32 in the bag is conducted to the patient 22 through the administration set 34.

Figure 2:
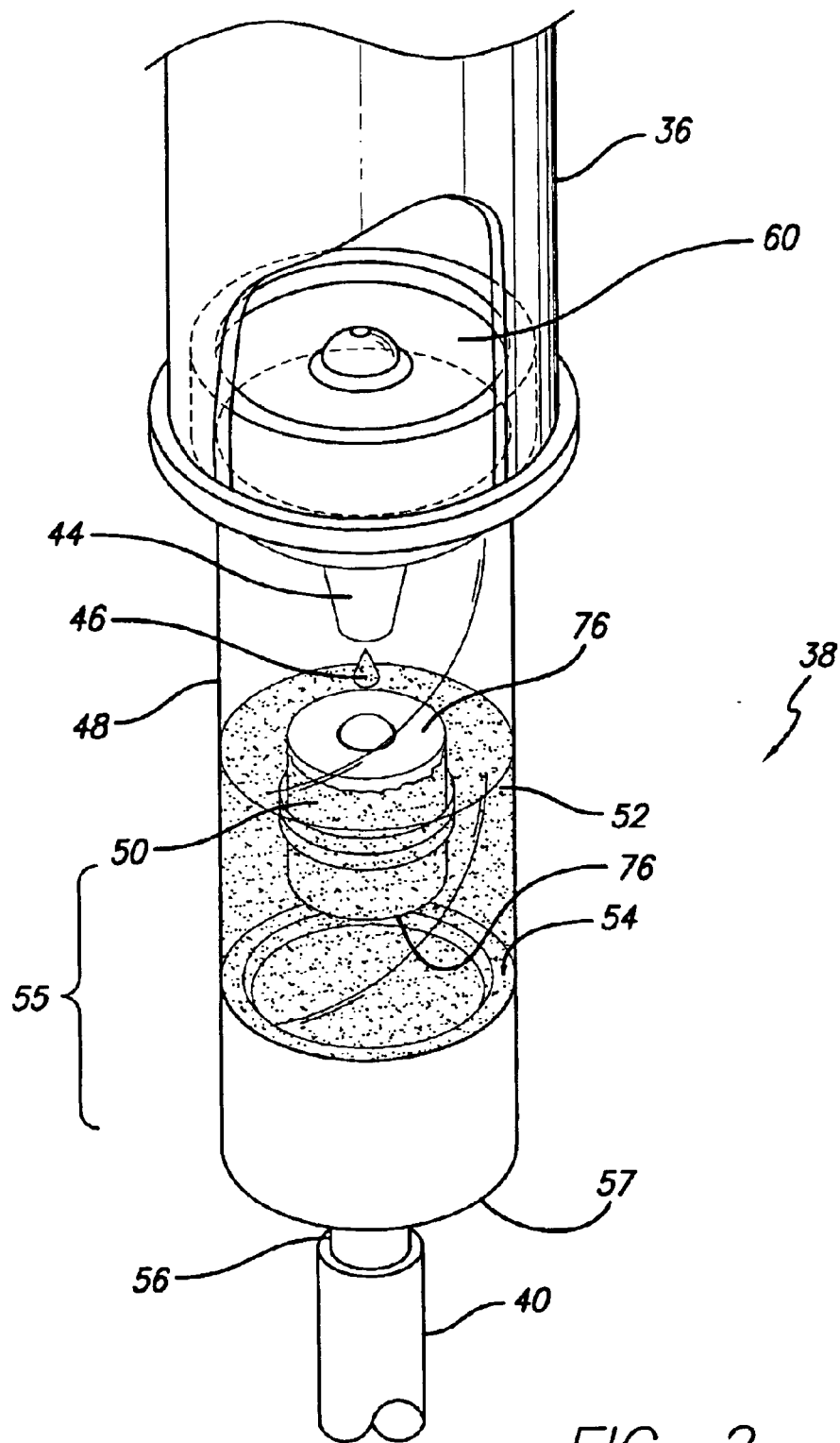
FIG. 2 is a partially cutaway, perspective view of a drip chamber mounted to a burette, the drip chamber having medical fluid therein, and showing a float having a buoyancy that causes the float to remain at or near the surface of the medical fluid in the drip chamber, the float providing a sealing surface, and the drip chamber having a valve seat in which the float is to seat when the fluid level in the chamber decreases to a certain level due to exhaustion of the fluid in the upstream burette or reservoir.

FIG. 2 is a perspective view of certain details of the drip chamber 38 in which is located a magnetically-activated shut off valve in accordance with aspects of the invention. As shown, the drip chamber is mounted to the downstream end of a burette 36 for this application although this is not required. The drip chamber 38 may instead have a sharpened spike for directly accessing the bag 24 of medical fluid. Such configurations for drip chambers are common. Additionally, in this embodiment, the magnetic automatic shut off valve is located in a drip chamber. However, the magnetic valve could be used in other fluid containers or conduits as well.

The drip chamber 38 includes a precise drop former 44 located at its upstream or proximal end operating to form drops 46 of a known size from the fluid in the burette 36 and permit those drops to fall into the transparent container 48 of the drip chamber 38. A float 50 is floating in the medical fluid 52 of the transparent container 48 due to its buoyancy. Downstream of the float 50 is a valve seat 54 in which the float will seat when the fluid 52 level lowers sufficiently. The float 50 and the valve seat 54 comprise a magnetic automatic shut off valve 55. The fluid level in the drip chamber 38 will vary depending on the amount of fluid remaining in the bag 24, in the upstream tubing 30, and in the burette 36 (see FIG. 1). As the level of fluid 52 decreases, the float 50 will approach closer and closer to the valve seat 54, eventually seating itself in the seat and shutting off flow through the drip chamber 38. The drip chamber also includes a downstream end 57 and defines an exit orifice 56 or outlet port at the downstream end to which the downstream tubing 40 is permanently attached in this embodiment. Also in this embodiment, the material used to form the transparent container 48 part of the drip chamber 38 is also used to form the exit orifice 56, although other arrangements may be used.

In the operation shown in FIG. 2, fluid from the bag 24 has flowed through the upstream tubing 30 and into the burette 36 where it is accumulated to the desired level. The inlet to the burette is then closed and the fluid allowed to exit through the exit port 60 of the burette into the drop former 44 of the drip chamber 38. The drop former forms precisely-sized drops that may be counted and timed to verify that a desired flow rate has been established with a variable clamp or other means (not shown). Because the fluid level in the transparent container 48 is high, the float 50 is above the valve seat 54 and fluid flows out the drip chamber 38 through the exit orifice 56 and through the downstream tubing 40 into the patient 22 (FIG. 1).

Figure 3:
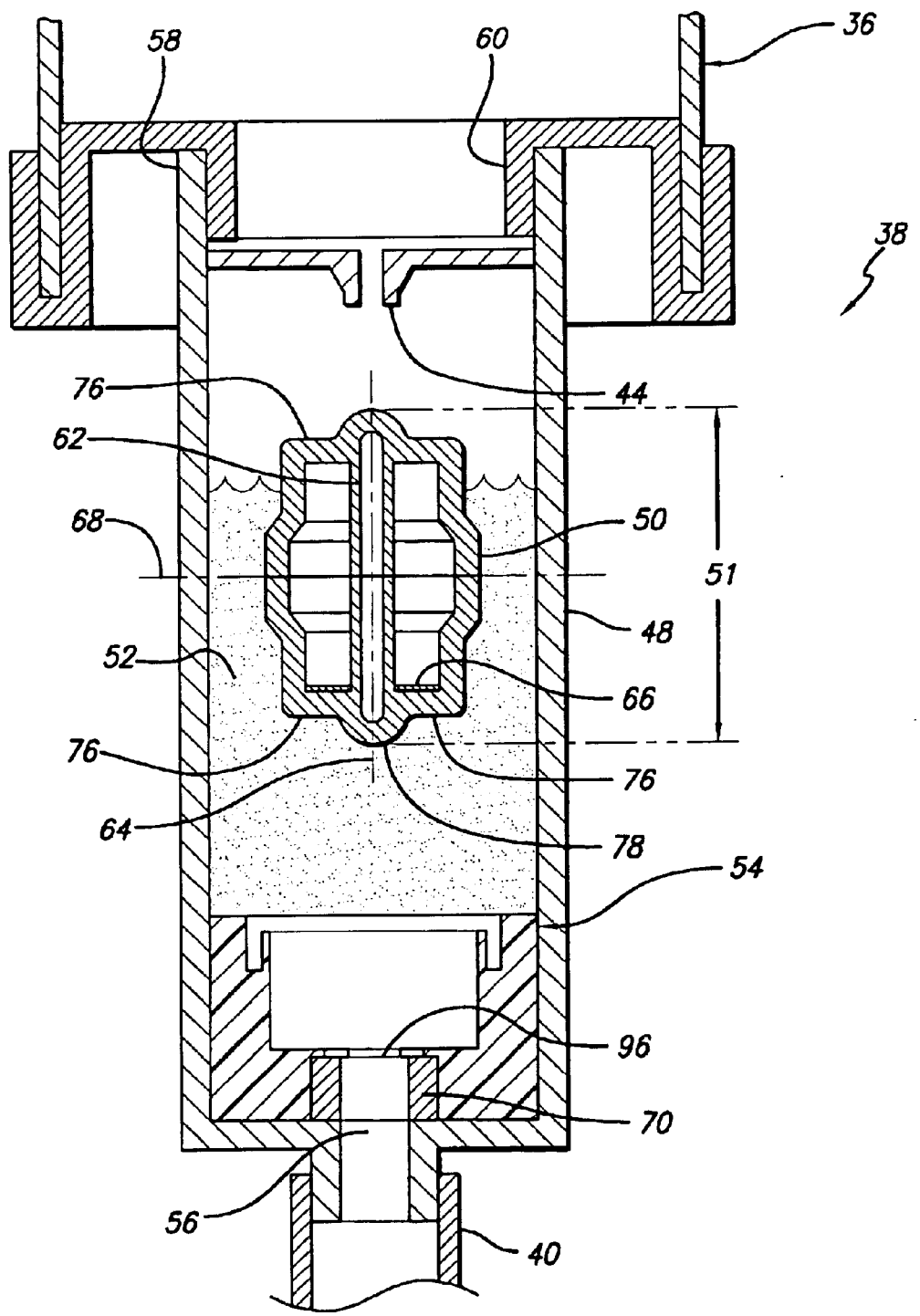
FIG. 3 is a cross-sectional view of the magnetic automatic shut off valve shown in FIG. 2 in accordance with aspects of the invention forming a part of a drip chamber that is located at the downstream end of a burette, the valve comprising a float suspended in the medical fluid in the transparent chamber of the drip chamber due its buoyancy developed in a higher fluid level, the float in this figure being unseated from the valve seat so that the medical fluid is being conducted to the patient through the drip chamber and the administration line.

Referring now to FIG. 3, the elements of FIG. 2 are shown in cross-sectional form. More detail is also shown of the downstream end of the burette 36. The input end, or upstream end 58 of the drip chamber 38 is connected, in this embodiment, directly to the output, or downstream, end 60 of the burette 36. The hollow float 50 is shown suspended in the fluid 52 of the drip chamber above the valve seat 54 due to the relatively high level of the fluid level 52 and the buoyancy of the float. The float 50, as shown in cross-section, defines an internal elongate post 62 which, in a preferred embodiment, is co-axially aligned with the longitudinal axis 64 of the float and extends from one end 76 of the float to the opposing end 76. Positioned about the post is a first magnetic attraction element 66 adapted to slide freely along the length of the post. In a preferred embodiment, the first attraction element 66 has an annular form with the inner diameter of that annular form being larger in diameter than the outer diameter of the post and the outer diameter of that annular form having a size smaller in diameter than the inner diameter of the hollow float 50 so that the first attraction element may freely slide along the post within the float. Together with the first attraction element 66, the float 50 is configured to be buoyant, and to float in medical fluid with its longitudinal axis 64 oriented generally vertically.

It will be appreciated that once the float 50 is inserted into the transparent container 48, no matter which end 76 is facing the exit orifice 56 gravity will cause the first magnetic attraction element 66 to fall toward the lower end of the float. In a preferred embodiment, the float 50 is rotationally symmetrical about its longitudinal axis 64 and is symmetrical about a plane perpendicular to the longitudinal axis and passing through its transverse center line which is indicated by a line 68 in FIG. 3. Because of this symmetry, the float may be initially assembled into the drip chamber with either end facing either direction. The internal first attraction element will simply fall to whichever end of the float is pointing down. This symmetry and freedom of the attraction element to move with gravity can lower manufacturing costs because fewer assembly errors will be made.

A second magnetic attraction element 70 is positioned at the valve seat 54 to attract the float 50 into a seating, and fluid shut off, position in the valve seat. In this case, the second magnetic attraction element 70 is located adjacent the exit orifice 56 of the drip chamber 38 and in alignment with the first attraction element 66 of the float when the float is centered in the drip chamber. In a preferred embodiment the second attraction element 70 also has an annular form. Preferably, the sizes of the annular forms of the first 66 and second 70 magnetic attraction elements are identical or substantially identical so that the lines of magnetic flux generated by either or both magnetic attraction elements directly impinge upon the other magnetic attraction element to create the maximum attraction force. At least one of the first and second magnetic attraction elements 66 and 70 comprises a magnet while the other element is formed either of a magnetic material that is attracted by a magnetic field, such as ferrous metal or the like, or is also a magnet. As one example, the second magnetic attraction element 70 may be an annular magnet while the first magnetic attraction element 66 may be a washer-type device or flat ring, containing a ferrous metal.

In another embodiment, both the first and second magnetic attraction elements may be magnets. However, in the second embodiment, assembly of the float into the drip chamber during manufacture would require that it be oriented such that unlike magnetic poles of the first and second magnetic attraction elements 66 and 70 face each other so that the float is attracted, rather than repelled, by the second element 70. It should be noted that both the first and second magnetic elements 66 and 70 are physically isolated from any medical fluid that flows through the drip chamber 38. Such fluid does not come into contact with either element. This may be accomplished by coating the magnetic elements with parylene or other water resistant material, or by mounting the magnetic elements within fluid-tight container elements. In the embodiment shown in these figures, the magnetic elements have been coated with parylene so that fluids are unable to reach the metallic surfaces of the magnetic elements. Also, the first magnetic attraction element 66 is located about the post 62 within the float 50, and the float 50 is sealed so that it will remain buoyant.

Figure 4:
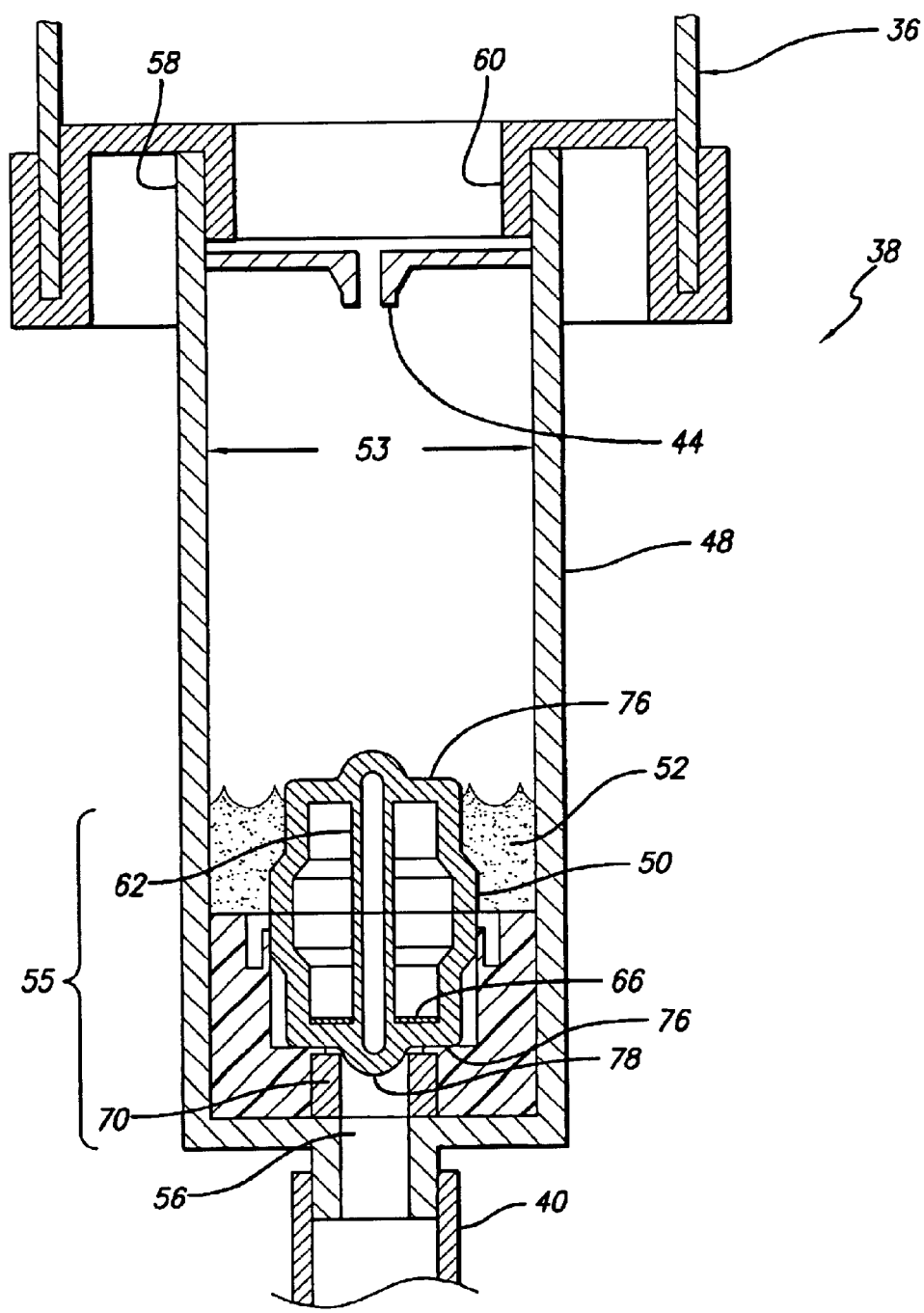
FIG. 4 is another cross-sectional view similar to that of FIG. 3 but showing the magnetic float seated in the magnetic valve seat in this figure due to a lower fluid level in the drip chamber, the float and valve seat combination blocking the flow of fluid, including air, through the drip chamber.

In the embodiment shown in FIG. 3, the transparent container 48 portion of the drip chamber 38 is relatively full of fluid 52 and the float 50 is buoyed to the fluid surface. The first attraction element 66 has fallen to the lower end of the post 62 in the float. It should be noted that the float has a length 51 and that the end of the float containing the first attraction element 66 is submerged with some volume of fluid 52 above it. Therefore when the submerged end of the float seats in the valve seat 54 shutting off flow, the fluid above its position at the valve seat will remain in the drip chamber. This is shown in FIG. 4. As is apparent then, the length 51 of the float (FIG. 3) and its buoyancy have an effect on the amount of fluid remaining in the drip chamber when the magnetic automatic valve 55 shuts off and may be selected to result in a desired amount of fluid remaining.

A similar effect is provided by the magnetic force developed by the first 66 and second 70 magnetic attraction elements. The stronger the force, the sooner the float 50 will seat leaving more fluid remaining in the drip chamber than if the magnetic force were weaker. Thus the strength of the magnetic force produced by the magnet (or magnets) may be selected so that the magnet will attract the float to the valve seat for shutting off flow when a selected level of fluid remains in the container.

Similarly, the strength of the magnetic force produced by the magnet may be selected so that the float will more readily align itself with the valve seat for automatic shutoff when the container is disposed at an angle other than vertical. The magnetic automatic shut off valve 55 will therefore be effective under a wider range of conditions of use of the drip chamber 38 than otherwise. For example, even in the case where the drip chamber is used during transport of the patient where the drip chamber may experience widely fluctuating tilt angles, the magnetic automatic shut off valve 55 will continue to function properly due to the strength of the magnetic attraction forces between the two magnetic parts 66 and 70 in the valve.

It should be noted that, in this embodiment, the length 51 of the float 50 (FIG. 3) exceeds the inner diameter 53 of the transparent container 48 (FIG. 4) of the drip chamber 38. Because of its length, the float is unable to rotate completely sideways in the drip chamber 38 and cannot wedge itself within the transparent container 48 thereby rendering the valve, of which it forms a part, inoperative. In more detail, the float 50 cannot rotate about the line 68 (FIG. 3) through the center of the float (perpendicular to the longitudinal axis) at an angle of ninety degrees in the transparent chamber 48.

As the fluid level 52 in the drip chamber 38 decreases, the float 50 will move closer and closer to the second magnetic attraction element 70 until the point is reached where the force of magnetic attraction between the first and second attraction elements 66 and 70 is greater than the upward force on the float caused by its buoyancy. At this point, the float will move into the position shown in FIG. 4 to seal off the flow of the remaining fluid 52 from the drip chamber 38 through the exit orifice 56. Because the float seats and seals the drip chamber before the fluid in the chamber is depleted, it prevents the entry of air into the downstream tubing 40. A beneficial effect is that the drip chamber 38 and downstream tubing remain primed.

Figure 5:
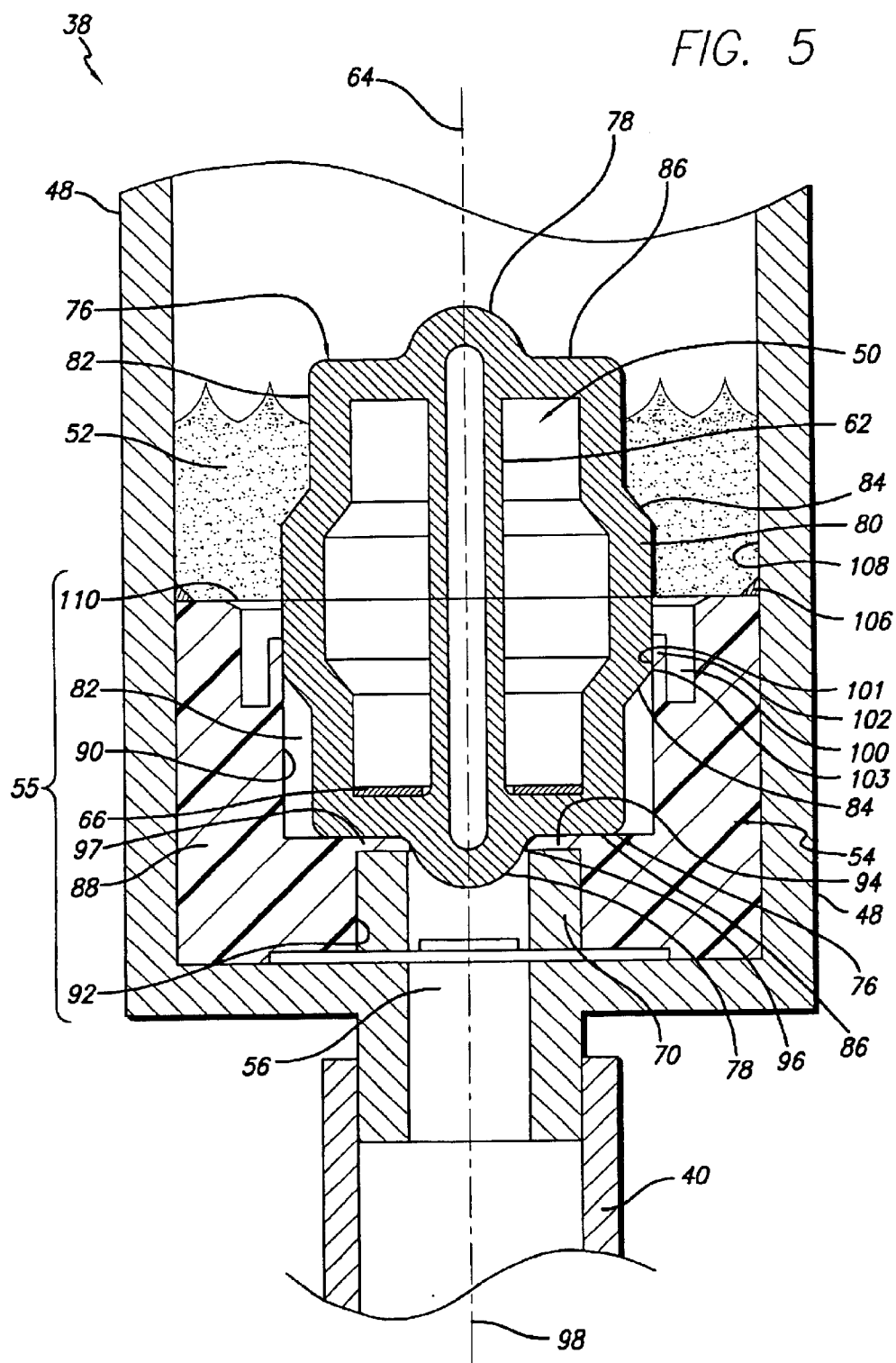
FIG. 5 is a larger scale, cross-sectional view of the float of FIGS. 3 and 4 seated in the valve seat in accordance with FIG. 4 and showing further detail.

Referring now to FIG. 5, an enlarged view of the float 50 engaged in a fluid seal configuration with the valve seat 54 is shown. It will be noted that the float in this embodiment includes two protruding portions 78 on opposing ends 76 that are rounded and each generally resembles a hemisphere. As mentioned above, the float has rotational symmetry about a vertical axis 64 which in FIG. 5, is coincident with the longitudinal axis 98 through the drip chamber 38. In the disclosed embodiment, the float also includes a cylindrical center section 80 having a larger diameter than two cylindrical end sections 82 which are also cylindrical in this embodiment. Taper portions 84 interconnect the center section 80 with each of the end sections 82. At the ends 76 of the float on which the protruding portions 78 are formed, a flat surface 86 surrounds each of the protruding portions and one or both form a sealing surface for interacting with the valve seat 54.

The valve seat 54 includes a cylindrically-shaped base 88 that has an outer diameter just smaller than the inner diameter of the transparent container 48 so that it may be slid into place within the container. It may be held in place with adhesive, a snap fit, or other means, as will be discussed below in more detail. However, it should be noted that the base 88 must make enough contact with the transparent container 48 portion of the drip chamber 38 so that the fluid in the chamber cannot flow around the outside of the base between it and the drip chamber and out the exit orifice 56 to thereby compromise the valve 55.

In this case, the base 88 is formed of a solid piece of material, such as silicone, and includes various relieved portions. A first relieved portion 90 is centered in the base 88 and has a diameter that is just equal to or smaller than the external diameter of the center section 80 of the float 50. It is deep enough to receive approximately one half of the length 51 of the float (FIG. 3) when the float 50 and base 88 are axially aligned, and therefore forms a float-receiving first outlet conduit portion. A second relieved portion 92 is formed in the base at a location distal to the first relieved portion 90 and has dimensions large enough in this embodiment to receive the entire annular magnet 70, which is a second magnetically attractive element. It will be noted from FIG. 5 that the first relieved portion 90 and second relieved portion 92 are both formed into the base 88 deeply enough so that a thin membrane 94 is left between them. A passage 96 is formed through the membrane 94 located between the first and second relieved portions so that fluid may flow between the first and second relieved portions and out the exit orifice 56 of the drip chamber. The combination of relieved portions 90 and 92 and the passage 96 through the first membrane 94 provides a fluid flow path out of the transparent container 48 portion of the drip chamber into the exit orifice 56 of the drip chamber.

In another embodiment (not shown), the first relieved portion 90 and the second relieved portion 92 may be formed deeply enough into the base 88 so that they interconnect and no membrane is left between them. Instead, a separate membrane component is mounted within the larger first relieved portion 90 to provide a sealing surface for the float. This separate membrane component would be thin, as in the embodiment shown in FIG. 5, and will function as does the membrane of FIG. 5. This separate membrane component may be fixed in position by adhesive, as an example.

The thickness of the membrane 94 is selected such that the membrane will provide an effective first sealing surface 97 that is oriented perpendicularly to the longitudinal center line 98 of the drip chamber 38 and will contact the flat surfaces 86 of the float ends 76 to form a fluid seal. In this case, the flat surfaces 86 of the float ends 76 are used to provide a second sealing surface to mate with the first sealing surface 97 of the valve seat and provide a first seal against fluid flowing out of the drip chamber.

The base 88 includes a third relieved portion 100 concentric with the first relieved portion 90 and comprises a narrow cut into the wall of the base 88 at a position radially outward of the first relieved portion 90. The location of the third relieved portion is selected to leave a thin piece of material 102 in the form of a second membrane to provide a third sealing surface 101 that will contact the center portion 80 of the float when the float is seated in the valve seat 54. The enlarged cylindrical portion 80 of the float therefore provides a fourth sealing surface 103 to mate with the third sealing surface 101 of the base 88 to provide a second seal against fluid leaving the drip chamber once the float has been located in the seat 54. The effect of this second seal provided by the third 101 and fourth 103 sealing surfaces is shown in FIGS. 4 and 5. In this case, the third sealing surface 101 is oriented in parallel with the longitudinal center line 98 of the drip chamber 38 and takes the form of a ring. It was found in one embodiment that the inner diameter of the first relieved portion 90 can be made to be slightly smaller than the outer diameter of the center section 80 of the float if the third relieved portion 100 is located such that the third sealing surface 101 is flexible enough to permit the float to properly seat. To obtain the necessary flexibility, the thickness of the second membrane 102 must be kept small and the narrow cut 100 must be deep enough so that the third sealing surface 101 will have the necessary flexibility to accommodate a slightly larger float 50. As shown in FIG. 5, the cut 100 is deeper than the depth that the enlarged diameter center cylindrical section 80 of the float 50 extends into the valve seat 54. This configuration provides flexibility to the third sealing surface 101.

It can be noted in FIGS. 4 and 5 that the lower protruding portion 78 of the float extends through the opening 96 in the first membrane 94 when the float is properly situated in the valve seat 54. Because it is rounded, the protruding portion 78 assists in guiding the float into sealing contact with the first sealing surface 97 so that a fluid-tight seal is made. As shown, the first thin membrane 94 and its first sealing surface 97 overhangs the annular magnet 70 in a cantilever arrangement with the magnet providing support for this portion of the first sealing surface 96. However, the first sealing surface 97 also overhangs the opening of the annular magnet by a certain amount and it has been found that this unsupported portion of the sealing surface 97 flexes under contact with the sealing surface 86 of the end 76 of the float and provides a better seal with the second sealing surface 86. In one embodiment, the ends 76 of the float 50 are formed of rigid thermoplastic polymer such as polypropylene and the first sealing membrane 94 is formed of flexible polymer such as thermoplastic elastomer or silicone. It has been found that these materials interact well to form an effective fluid seal. In one embodiment, the thickness of the first sealing membrane 94 was 0.5–0.75 mm (0.02–0.03 inches).

It will be appreciated that in three dimensions the first and third described sealing surfaces 97 and 101 may produce a generally annular configuration, with one edge of the annulus of both connected to, or part of, respective areas of the base 88 and the other edge free to bend should the float 50 exert a force thereon while being magnetically drawn into contact with the base. By selecting appropriate thicknesses for the first and third sealing surfaces, the desired flexible contact and resulting seal between the transparent container 48 and the float 50 can be obtained. Although shown as being formed from the base 88, it will be appreciated that the first and third sealing surfaces described above may be formed of independent components introduced into the container in the form of membranes to be held by one edge, and are not limited to forming part of a unitary component of any other portion of the stop-valve.

With continuing reference to FIG. 5, the base 88 in this embodiment includes a locking ring 106 formed on the inner wall 108 of the transparent container 48. The locking ring is ramped towards the downstream direction but is perpendicular to the wall 108 in the upstream direction. The base 88 and magnet 70 combination may be slid into the transparent container 48 and over the locking ring during assembly and will be held in position as shown in FIG. 5 by the locking ring. FIG. 5 also shows that the second sealing membrane 102 is located at a more distal position than the more radially outward portion of the base 88, which would permit the inclusion of a taper 110 leading to the second sealing lip 102.

Figure 6:
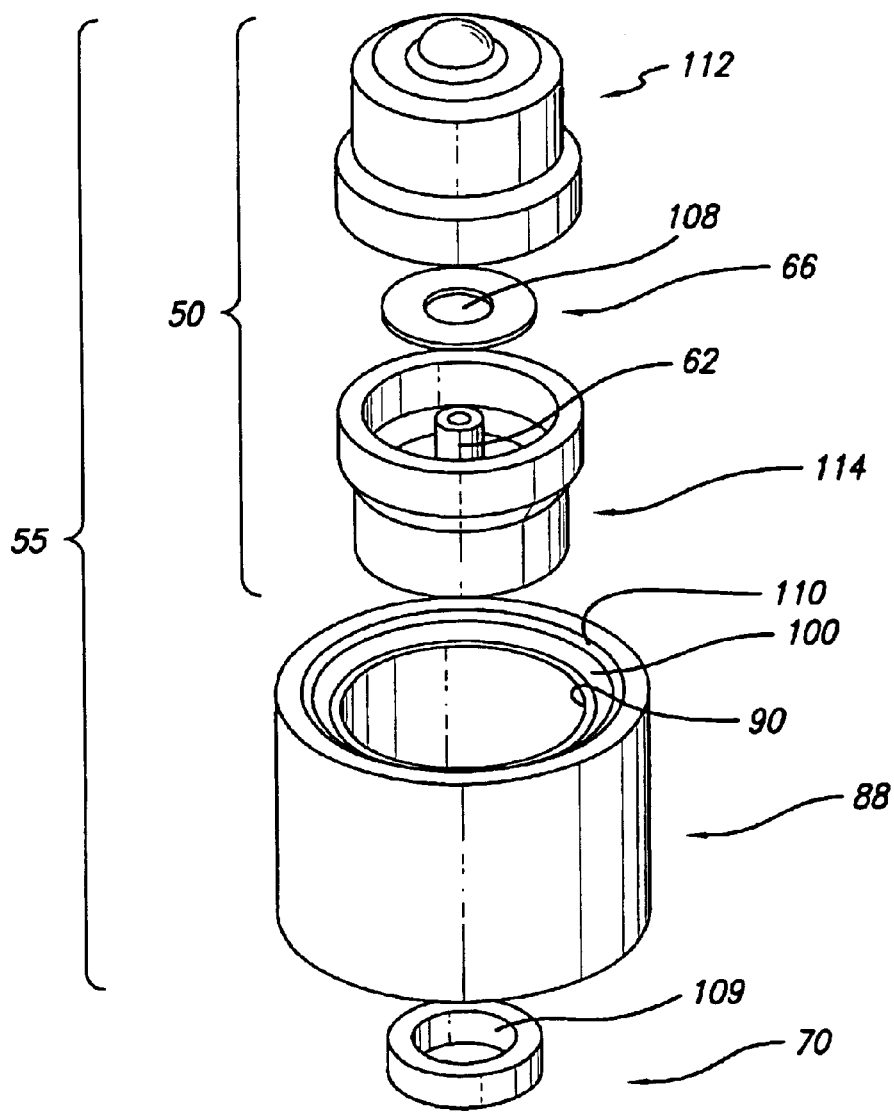
FIG. 6 is an exploded perspective view of a magnetic automatic shut off valve in accordance with aspects of the invention showing an exploded view of the float of FIGS. 2 through 5 in which a portion of the inner mounting post used for mounting the magnetic element can be seen, the figure also showing the valve seat and an annular magnet forming a part of the valve seat used to attract the float to the valve seat.

Referring now to FIG. 6, a perspective exploded view of a magnetic automatic flow stop 55 in accordance with aspects of the invention is shown. The float 50 comprises first and second identical float portions 112 and 114 or halves, each of which has one-half the inner post 62. Before assembling the first and second float portions, the first attractive element 66, which in this case is a washer formed of magnetically attractive material, is mounted on one of the post halves. The two float portions may then be permanently assembled together such as by adhesive, or ultrasonic welding, or with other means such as spin welding.

FIG. 6 further shows an embodiment of a base 88 having a first relieved portion 90, a third relieved portion 100, and a taper 110 from the outer wall to the third relieved portion. The second attractive element 70 is shown, which in this case is a magnet, and although the second relieved portion of the base is not shown in this view, it is identical to that shown in FIG. 5. The magnet 70 would therefore slide up and into the distal end, or downstream end, of the base into the second relieved portion (92 shown in FIG. 5). In this embodiment, the outer diameter of the magnet 70 is identical or substantially the same as the outer diameter of the washer 66, and when the float is properly seated in the valve seat as shown in FIG. 5, the washer 66 and magnet 70 will be aligned with each other. Additionally, the aperture 108 of the washer and the aperture 109 of the magnet will also be aligned with each other and in this embodiment, have approximately the same diameter. This matching of physical characteristics and alignment will result in the more efficient use of the magnetic attraction force provided by the magnet 70, so that a smaller magnet can be used with commensurate lower manufacturing costs.

In use, operation of the magnetic automatic shut off valve 55 may commence with the fluid container 24 being accessed and the administration set 34 primed. A selected amount of fluid is allowed to flow into the burette 36. The burette is then closed and fluid permitted to flow from the burette output port 60 into the drip chamber 38. The float is dislodged from the valve seat 54 by mechanical means, such as by squeezing the side of the transparent container 48 at the valve seat thereby overcoming the magnetic force holding it in a sealed position in the seat 54. The float will then rise with the fluid level in the drip chamber opening the exit orifice 56 so that fluid may flow to the patient 22. As the measured amount of fluid in the burette is exhausted, the fluid level in the drip chamber 38 will become depleted and the magnetic force between the first and second magnetic attraction elements 66 and 70 will cause the float to seal off the exit orifice 56 of the drip chamber and flow through the fluid administration set 34 will cease. Because the length 51 of the float 50 exceeds the inner diameter 53 of the drip chamber, it will not become wedged in the transparent container 48 of the drip chamber even if the drip chamber is not level or is being moved due to patient activity or transport. Additionally, the float will be strongly attracted into proper alignment with the first relieved portion 90 of the valve seat 54 due to the magnetic force developed by the centrally-located magnet 70. Additionally, if the float were to become oriented at an angle to the valve seat 54, the tapered sections 86 between the cylindrical sections of the float would act as guides to re-orient the float into a correct alignment with the first relieved portion 90 of the valve seat upon meeting the taper 110 of the wall (see FIG. 5). Further, the float has beveled or rounded edges to assist in properly locating it in the valve seat. The prime in the fluid administration set is preserved and this feature of the stop-valve 55 will allow the burette to be refilled with fluid and an infusion to begin again without having to re-prime the set 34.

Figure 7:
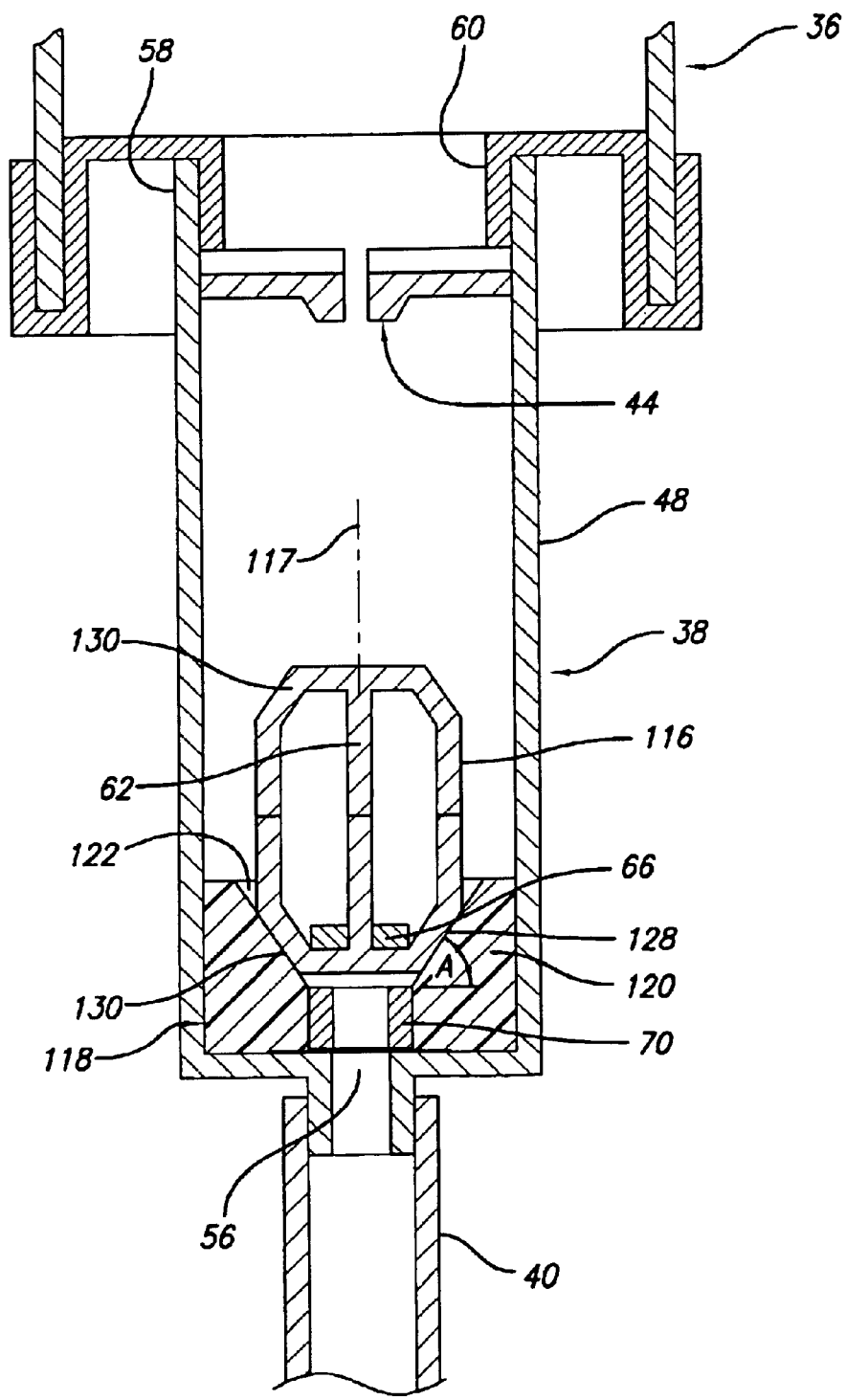
FIG. 7 is a cross-sectional view similar to that of FIG. 4 showing an alternate embodiment of a magnetic float and a valve seat, with the float in the flow shut off position thereby preventing the flow of fluid through the drip chamber and the administration set.

In another embodiment of a float and valve seat combination as shown in FIG. 7, the float 116 continues to be rotationally symmetrical about its longitudinal axis 117 to aid in manufacturing and assembling the drip chamber, and continues to comprise an internal post 62 on which the first magnetic element 66 is slidably mounted. The drip chamber 38 also comprises a valve seat 118 formed of a base 120; however, in this embodiment, the base 120 differs from the base shown in FIG. 5. The base 120 comprises a first relieved portion 122 that is angled in this case. A second relieved portion 124 is provided as in the previous embodiment and once again connects with the exit orifice 56. However, the first and second relieved portions are interconnected with no membrane in between. The second magnetically attractive element 70 is located in the second relieved portion 124 as in the previous embodiment.

In this case, such a membrane is not required due to the increased surface area provided by the first relieved portion 122. As shown in FIG. 7, the first relieved portion 124 at the upstream end of the base 120 has a different configuration from the base of FIG. 5. In the embodiment of FIG. 7, the first relieved portion is tapered at an approximate angle (shown as "A" in FIG. 7) of 70 degrees providing a first sealing surface 126 opening into a passage 128 through the base that connects the transparent container 48 with the exit orifice 56 to allow fluid flow out of the drip chamber 38. The float 116 also includes a tapered sealing surface 130 forming a second sealing surface that is complementary to the taper and sealing surface 126 of the valve seat 118. In the embodiment shown in FIG. 7, the tapered sealing surface 130 of the float has a frusto-conical shape. In this embodiment, the end tips 132 of the float 116 are shown flat but may have other shapes, such as round or pointed.

The sealing surface shapes 124 and 130 of the embodiment of FIG. 7 have an advantage in that they provide a larger overall sealing surface area and a membrane or membranes such as that shown in FIG. 5 are not needed.

Referring now to FIG. 8, a cross sectional shape of the distal end 150 of a drip chamber 152 is shown. A valve seat 154 seal and retaining arrangement is shown comprising inward protrusions 156 from the inner wall 158 of the drip chamber with selectively located grooves 160 formed in the outer surface 162 of the valve seat 154. A first distal groove 164 is formed in the valve seat that coincides with a first protrusion 166 on the inner wall of the drip chamber. This, and a second groove 168 on the valve seat and a second protrusion 170 on the wall 158 serve to engage two protrusions from the drip chamber wall and retain the valve seat 154 in the desired position in the drip chamber. The protrusions from the drip chamber wall take the form of rings in this embodiment. The grooves of the valve seat are also formed completely around the valve seat so that ease in manufacturing results. More or fewer protrusions and grooves may be used in other embodiments.

In FIG. 8, a third groove 172 formed at the proximal end of the valve seat leaves a raised ring 174 on the valve seat that will contact the inner wall 158 of the drip chamber and form a fluid seal 176. This fluid seal 176 will prevent fluid from flowing around the outside of the valve seat and out the outlet port 56.

FIG. 9 presents an external perspective view of only the valve seat 154 of FIG. 8 showing the grooves and first relieved portion 90. FIG. 10 shows in an exaggerated way the taper of the drip chamber 152. The angle of taper is indicated by numeral 190. The taper not only aids in molding the drip chamber but also aids in inserting the valve seat 154.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. An automatic shut off valve for use in regulating the flow of medical fluid, comprising:
    a container adapted to contain medical fluid, the container having an upstream end and a downstream end and defining an exit orifice at the downstream end;
    a hollow float defining an internal post, the float disposed within the container;
    a first attraction element disposed within the float and disposed over the post and adapted to slide along the post; and
    a second attraction element disposed at the exit orifice, the first and the second attraction elements being formed of materials that produce magnetic attraction between the two elements;
    wherein the materials that produce the magnetic attraction between the two elements are selected so that the strength of the magnetic attraction between the two elements is such that when the fluid in the container falls to a level near depletion, the first and second attraction elements are attracted to each other with sufficient force to move the float into a position that seals the downstream end against fluid flow.

2. The automatic shut off valve of claim 1 further comprising:
    a valve seat located proximate the exit orifice at the downstream end of the container, the valve seat having a first sealing surface;
    wherein the float includes a second sealing surface configured to mate with the first sealing surface and form the seal against fluid flow.

3. The automatic shut off valve of claim 2 further comprising:

a third sealing surface disposed at a fixed position within the container at a selected location away from the first sealing surface; and a fourth sealing surface located on the float and configured to mate with the third sealing surface to provide a greater seal against fluid flow.

4. The automatic shut off valve of claim 3 wherein the float has a section of increased diameter that forms the fourth sealing surface.

5. The automatic shut off valve of claim 4 wherein the section of increased diameter forming the third sealing surface is located substantially at the center of the float.

6. The automatic shut off valve of claim 3 wherein the third sealing surface comprises a membrane of pliable material formed substantially in the shape of a ring and having a smaller inner diameter than an outer diameter of the fourth sealing surface of the float wherein the third sealing surface and the fourth sealing surface come into contact with each other thereby sealing against fluid flow when the float is disposed such that the first and second sealing surfaces are in contact.

7. The automatic shut off valve of claim 1 further comprising:

a first sealing surface disposed at a fixed position within the container proximate the exit orifice at the downstream end of the container; and a third sealing surface disposed at a fixed position within the container on a container wall at a selected location away from the first sealing surface;

wherein the first and third sealing surfaces engage the float to form seals against fluid flow when the float is moved into the position that seals the downstream end against fluid flow due to the magnetic attraction between the two elements.

8. The automatic shut off valve of claim 7 wherein:

the float includes opposite ends, each end of which includes a second sealing surface configured to mate with the first sealing surface; and the float includes a generally cylindrical section that provides a fourth sealing surface configured to mate with the third sealing surface;

wherein the first and second sealing surfaces form a seal against flow and the third and fourth sealing surfaces form another seal against flow when the float has been moved into the position that seals the downstream end against fluid flow due to the magnetic attraction between the two elements.

9. The automatic shut off valve of claim 1 wherein the float comprises two substantially identical halves joined together to form the float, each float half including a half of the post such that when the substantially identical float halves are joined together, the entire internal post is formed.

10. The automatic shut off valve of claim 9 wherein:

the float is generally cylindrical with a larger diameter cylindrical section located at the longitudinal center of the float;

the float includes opposing ends; and the first attraction element is disposed over the post such that it may freely slide along the post;

whereby the float may be inserted into the container with either of the opposing ends facing the exit orifice at the downstream end of the container and the first attraction element will slide along the internal post towards the second attraction element to establish a magnetic interaction with the second attraction element.

11. The automatic shut off valve of claim 10 wherein:

the first attraction element has an inner opening larger in diameter than the diameter of the post; and the outer diameter of the first attraction element has a size that is smaller than the inner diameter of the hollow float;

whereby the first attraction element is free to slide along the post within the float.

12. The automatic shut off valve of claim 1 wherein the float has a length that exceeds an inner diameter of the container.

13. The automatic shut off valve of claim 1 wherein at least one of the first and second attraction elements comprises a magnet with the strength of the magnetic force produced by the magnet selected so that the magnet will attract the float to the valve seat for shutting off flow when a selected level of fluid remains in the container.

14. The automatic shut off valve of claim 13 wherein the strength of the magnetic force produced by the magnet is selected so that the float will align itself with the valve seat when the container is disposed at an angle other than vertical.

15. The automatic shut off valve of claim 1 wherein at least one of the first and second attraction elements comprises a magnet with the strength of the magnetic force produced by the magnet selected so that the float will align itself with the valve seat when the container is disposed at an angle other than vertical.

16. The automatic shut off valve of claim 1 wherein the float has a longitudinal axis and is rotationally symmetrical about the longitudinal axis.

17. The automatic shut off valve of claim 1 wherein the float is symmetric al about a plane perpendicular to the float's longitudinal axis, the plane being located through the center of the float.

18. An automatic shut off valve for use in regulating the flow of medical fluid, comprising:

a container adapted to contain medical fluid, the container having an upstream end and a downstream end and defining an exit orifice at the downstream end;

a hollow float defining an internal post, the float disposed within the container, wherein the float comprises two substantially identical halves joined together to form the float, each float half including a half of the post such that when the substantially identical float halves are joined together, the entire internal post is formed;

a first attraction element disposed within the float and disposed over the post and adapted to slide along the post; and a second attraction element disposed at the exit orifice, the first and the second attraction elements being formed of materials that produce magnetic attraction between the two elements;

wherein the materials that produce the magnetic attraction between the two elements are selected so that the strength of the magnetic attraction between the two elements is such that when the fluid in the container falls to a level near depletion, the first and second attraction elements are attracted to each other with sufficient force to move the float into a position that seals the downstream end against fluid flow;

wherein the float is generally cylindrical with a larger diameter cylindrical section located at a longitudinal center of the float;

the float includes opposing ends; and the first attraction element is disposed over the post such that it may freely slide along the post towards each of the opposing ends;

whereby the float may be inserted into the container with either of the opposing ends facing the exit orifice at the downstream end of the container and the first attraction element will slide along the internal post towards the second attraction element to establish a magnetic interaction with the second attraction element.

19. The automatic shut off valve of claim 18 wherein at least one of the first and second attraction elements comprises a magnet with the strength of the magnetic force produced by the magnet selected so that the float will align itself with the valve seat when the container is disposed at an angle other than vertical.

20. The automatic shut off valve of claim 18 wherein the float has a longitudinal axis and is rotationally symmetrical about the longitudinal axis.

21. The automatic shut off valve of claim 18 wherein the float is symmetrical about a plane perpendicular to the float's longitudinal axis, the plane being located through the center of the float.

22. The automatic shut off valve of claim 18 further comprising:

a first sealing surface disposed at a fixed position within the container proximate the exit orifice at the downstream end of the container; and a third sealing surface disposed at a fixed position within the container on a container wall at a selected location away from the first sealing surface;

wherein the first and third sealing surfaces engage the float to form seals against fluid flow when the float is moved into the position that seals the downstream end against fluid flow due to the magnetic attraction between the two elements.

23. The automatic shut off valve of claim 22 wherein:

the float includes opposite ends, each end of which includes a second sealing surface configured to mate with the first sealing surface; and the float includes a generally cylindrical section that provides a fourth sealing surface configured to mate with the third sealing surface;

wherein the first and second sealing surfaces form a seal against flow and the third and fourth sealing surfaces form another seal against flow when the float has been moved into the position that seals the downstream end against fluid flow due to the magnetic attraction between the two elements.

24. A method of automatically shutting off the flow of medical fluid from a container having an upstream end and a downstream end and defining an exit orifice at the downstream end, said method comprising:

disposing a first attraction element over a post disposed within a hollow float so that the first attraction element may slide freely along the post;

disposing a second attraction element at the exit orifice, the first attraction element and the second attraction element being formed from materials that produce magnetic attraction between the two elements; and inserting the float into the container so that, when fluid in the container falls to a level near depletion, the first and second attraction elements are attracted to each other with sufficient force to move the float into a position that seals the downstream end to fluid flow.

25. The method of automatically shutting off the flow of medical fluid of claim 24 further comprising:

forming the float from two substantially identical halves joined together, each float half including a half of the post such that when the substantially identical float halves are joined together, the entire internal post is formed.

26. The method of automatically shutting off the flow of medical fluid of claim 24 further comprising:

forming the float to be generally cylindrical with a larger diameter cylindrical section located at the longitudinal center, and with the float having opposing ends; and disposing the first attraction element over the post such that the first attraction element may freely slide along the post;

whereby the float may be inserted into the container with either of the opposing ends facing the exit orifice at the downstream end of the container and the first attraction element will slide along the internal post towards the second attraction element to establish a magnetic interaction with the second attraction element.

27. The method of automatically shutting off the flow of medical fluid of claim 24 further comprising:

forming the float to have a length that exceeds an inner diameter of the container.

28. The method of automatically shutting off the flow of medical fluid of claim 24 further comprising:

forming the first and second attraction elements so that at least one comprises a magnet; and selecting the strength of the magnetic force produced by the magnet so that the magnet will attract the float to the valve seat for shutting off flow when a selected level of fluid remains in the container.

29. The method of automatically shutting off the flow of medical fluid of claim 28 further comprising:

selecting the strength of the magnetic force produced by the magnet to align the float with the valve seat when the container is disposed at an angle other than vertical.

30. The method of automatically shutting off the flow of medical fluid of claim 24 further comprising:

forming the float such that it is rotationally symmetrical about a longitudinal axis.

31. The method of automatically shutting off the flow of medical fluid of claim 24 further comprising:

forming the float such that it is symmetrical about a plane perpendicular to the float's longitudinal axis, the plane being located through the center of the float.

* * * * *

UNITED STATES PATENT AND TRADEMARK OFFICE
CERTIFICATE OF CORRECTION

PATENT NO.   : 6,695,004 B1
DATED        : February 24, 2004
INVENTOR(S)  : John L. Raybuck It is certified that error appears in the above-identified patent and that said Letters Patent is hereby corrected as shown below:

Column 16,
Line 33, delete "symmetric al" and insert -- symmetrical --.

Signed and Sealed this

Tenth Day of August, 2004

JON W. DUDAS
*Acting Director of the United States Patent and Trademark Office*